United States Patent [19]
Kremer

[11] Patent Number: 6,139,560
[45] Date of Patent: Oct. 31, 2000

[54] CUTTING DEVICE AND METHOD FOR MAKING CONTROLLED SURGICAL INCISIONS

[76] Inventor: Frederic B. Kremer, 887 Roscommon Rd., Bryn Mawr, Pa. 19010

[21] Appl. No.: 09/268,802

[22] Filed: Mar. 16, 1999

[51] Int. Cl.⁷ ...................................................... A61F 9/00
[52] U.S. Cl. ......................... 606/166; 606/107; 606/167
[58] Field of Search ................................ 606/1, 107, 166, 606/167, 185; 604/19, 22

[56] References Cited

U.S. PATENT DOCUMENTS

| | | |
|---|---|---|
| 4,180,075 | 12/1979 | Marinoff . |
| 4,662,370 | 5/1987 | Hoffman et al. ........................ 606/166 |
| 5,080,111 | 1/1992 | Pallin . |
| 5,370,652 | 12/1994 | Kellan ...................................... 606/166 |
| 5,876,415 | 3/1999 | Pierce et al. ............................. 606/166 |

*Primary Examiner*—Glenn K. Dawson
*Attorney, Agent, or Firm*—Seidel, Gonda, Lavorgna & Monaco, PC

[57] ABSTRACT

A surgical cutting device for making incisions in tissue has a holder with a distal end, an applanation plate extending from said distal end for contacting and altering the contour of tissue to be incised, and a cutting blade reciprocally movable with respect to the holder and extending from said distal end in proximity to the applanation plate. The blade is guided by the holder and linearly advanceable into the tissue to effect an incision. After the incision is made, the blade is retractable from the tissue.

4 Claims, 6 Drawing Sheets

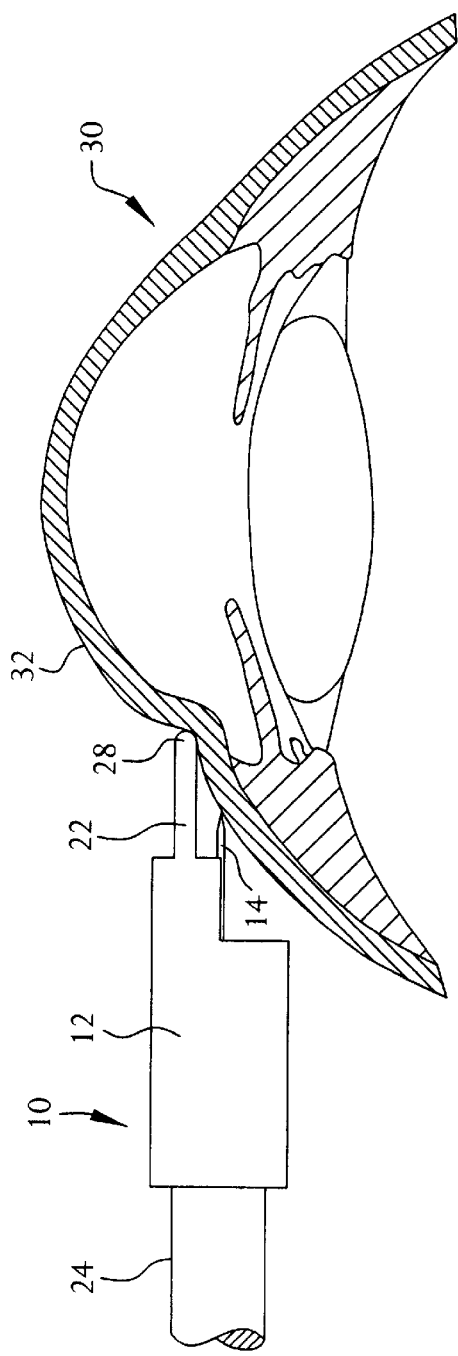
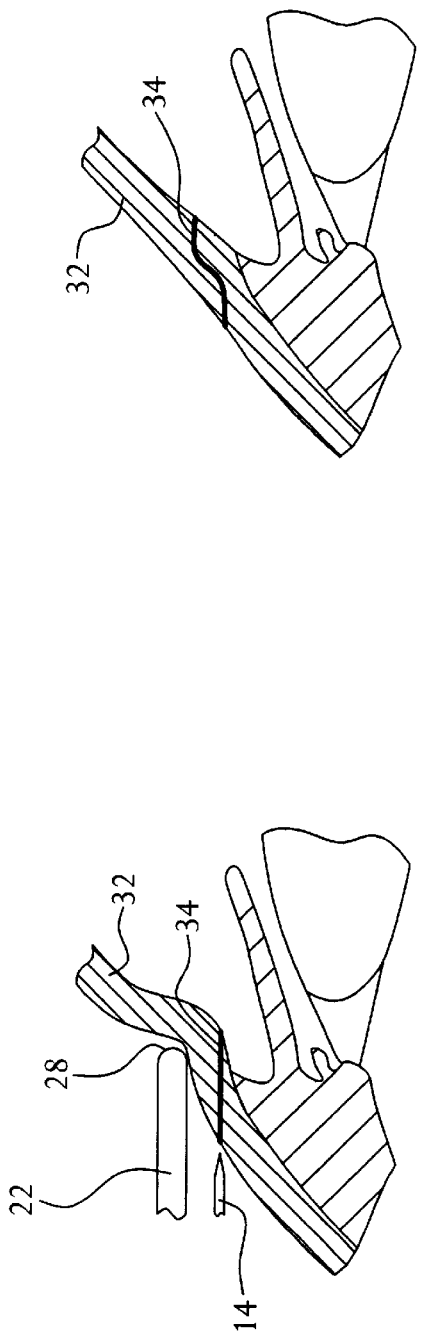
FIG. 6
FIG. 7
FIG. 8

CUTTING DEVICE AND METHOD FOR MAKING CONTROLLED SURGICAL INCISIONS

FIELD OF THE INVENTION

The present invention relates to cutting devices, in particular cutting devices for making controlled surgical incisions. The present invention is useful in ophthalmic surgery, but is not limited to specific surgical procedures.

BACKGROUND OF THE INVENTION

A cataract is an opacity of the lens of the eye. Cataracts may be congenital or may occur as a result of trauma or, less commonly, systemic disease. Senile cataract is by far the most common type, and most people over sixty have some degree of lens opacity.

A cataractous lens, or one which has become partially or wholly opaque, sometimes requires removal from the eye, and replacement with an intraocular lens. Whether to remove the lens depends upon a variety of factors taken into consideration by the ophthalmic surgeon. If a decision is made to remove the lens, the surgeon has a choice of several techniques. In some instances a lens implant may be placed in the eye without removing the natural lens of the eye.

In the conventional cataract extraction technique, a conjunctive flap is formed by making an incision in the conjunctiva so that it can be moved back to expose the sclera of the eye at the corneal border. In order to obtain access to the cataractous lens, which is located behind the cornea, an incision is made extending around the cornea in the limbus area, a short distance (between about zero to two millimeters) from the periphery of the cornea and extending between approximately 3.0 and 6.0 mm. One of the more desirable types of incisions is a multiplane incision, or "stepped" incision, in which a first cut, in a first plane, extends only partially through the cornea. This partial thickness incision has been referred to as a "cataract groove." Second, and sometimes third, cuts, in second and third planes, are then made to enter the anterior chamber for access to the lens.

The first incision typically extends to a depth of approximately one-half the thickness of the wall of the eye globe, and is made by use of a scalpel blade, razor blade, or other instrument, held freehand either perpendicular to the wall of the eye globe or at an angle to it. The first incision may be enlarged with either a scissor, keratome, or other blade implement. Once the entire incision is completed, the cornea can be lifted or retracted to gain access to the anterior chamber. The cataractous lens can then be removed.

The multiplane, or "stepped," incision has a number of advantages over an incision which lies in a single plane and extends through the full thickness of the eye into the anterior chamber. With a single plane incision, there is a tendency for fluid to leak through the incision, requiring the use of sutures. With a stepped incision, however, there is a tendency for the incision to seal itself, obviating the need for sutures.

Prior to the present invention, the first cut in a stepped incision has been formed freehand by the surgeon. No matter how skilled the surgeon may be, it is difficult to make the cut with precision. No two incisions will ever be exactly the same, and hence results and post operative effects vary. In addition, the surgeon often encounters difficulty in completing the full incision, since the cutting edge is usually supported in a holder gripped by the surgeon in one hand while he stabilizes the globe of the eye with a fixator or forceps in the other hand. Accordingly, it is necessary for the surgeon to both rotate the globe of the eye using the fixator in one hand while rotating the position of the cutting edge with the other hand. The surgeon often finds himself in an awkward position and unable to complete the cut in a single sweeping motion. This can result in a cut which is not smooth, or may not be positioned in the desired location.

It is an object of the present invention to provide a cutting device for making a stepped incision in a single linear, reciprocal stroke of a guided cutting edge, so that it is unnecessary for a surgeon to make the cut freehand.

The invention reduces the level of surgical skill required, and provides a more consistent, better sealing, and faster healing incision.

SUMMARY OF THE INVENTION

In its broad aspect, the invention is a surgical cutting device comprising a tissue contact member for contacting and altering the contour of tissue to be incised and a cutting blade movable linearly toward and away from said tissue in a plane spaced from the tissue contact member by a preselected distance.

A first embodiment of the present invention includes a surgical cutting device comprising a holder having a distal end, an applanation plate extending from said distal end for contacting and altering the contour of tissue to be incised, and a cutting blade reciprocally movable with respect to the holder and extending from said distal end in proximity to the applanation plate. The blade is guided by the holder and is linearly advanceable into said tissue to effect an incision and retractable therefrom after the incision is made.

A second embodiment of the present invention includes a vacuum ring including an inner contact wall and an outer housing wall. The contact wall and the housing wall form a hollow chamber between them. The contact wall includes an applanation section extending from it for contacting and altering the contour of tissue to be incised. A holder extends from the housing wall, and a cutting blade moves reciprocally and linearly with respect to the holder and is guided by it, through a passageway in the contact wall and into the tissue. The blade effects an incision in the tissue in proximity to the applanation section.

The present invention also includes a method of making a surgical incision, comprising the steps of altering the pre-incision contour of tissue to be incised by applying pressure to said tissue using a tissue contact member, linearly advancing a cutting blade into said tissue adjacent the tissue contact member to effect a linear incision, retracting the cutting blade from the incised tissue, and removing the applied pressure from the tissue and allowing the tissue to return to its pre-incision contour.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 6 is a view of a cutting device according to the invention being used to incise the cornea of an eye.

FIG. 7 illustrates a linear incision effected in the cornea by the present invention, after the blade has been retracted and while the applanation plate is still in contact with the eye.

FIG. 8 illustrates the shape of the incision of FIG. 7 after the applanation plate has been removed and the eye allowed to return to its preincision contour.

DESCRIPTION OF THE INVENTION

Figure 1:
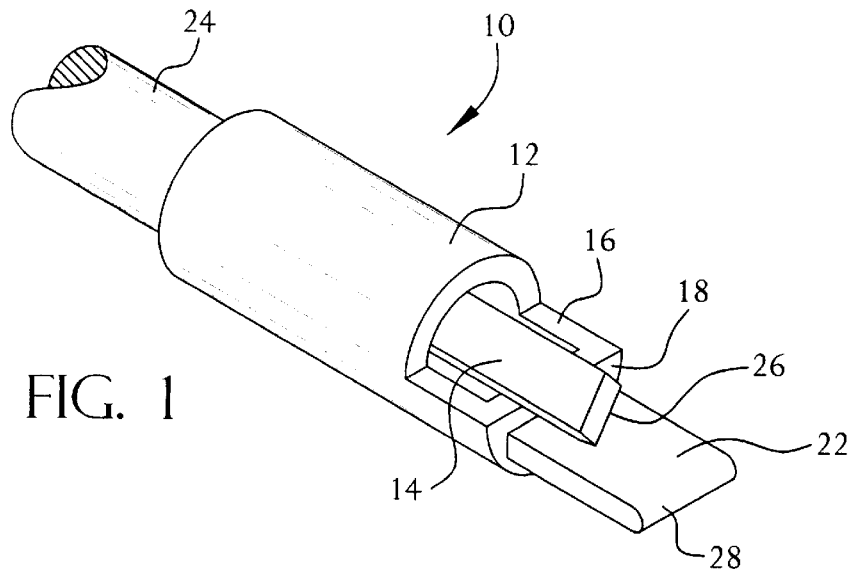
FIG. 1 is an isometric view of a first embodiment of a surgical cutting device according to the present invention, showing the holder, applanation plate, and cutting blade.

Referring now to the drawings, wherein like numerals indicate like elements, there is shown in FIG. 1 a surgical cutting device 10 according to a first embodiment of the present invention. The cutting device 10 comprises a holder 12 and a cutting blade 14. The holder 12 is in the form of a hollow cylindrical tube, although the holder 12 may have other convenient shapes without departing from the invention. The surface of the holder 12 may, if desired, be knurled or engraved in order to assist the surgeon in grasping the holder and preventing it from slipping during use. The holder 12 has a rabbet 16 at its distal end 18, which forms a step 20. Spaced from the step 20 and extending outwardly from the distal end 18 of the holder 12 is a tissue contact member in the form of an applanation plate 22 for contacting tissue to be incised by the cutting blade 14. The step 20 serves to control the spacing between the cutting blade 14 and the applanation plate 22 which, in turn, controls the depth of the incision relative to the tissue being incised.

Figure 2:
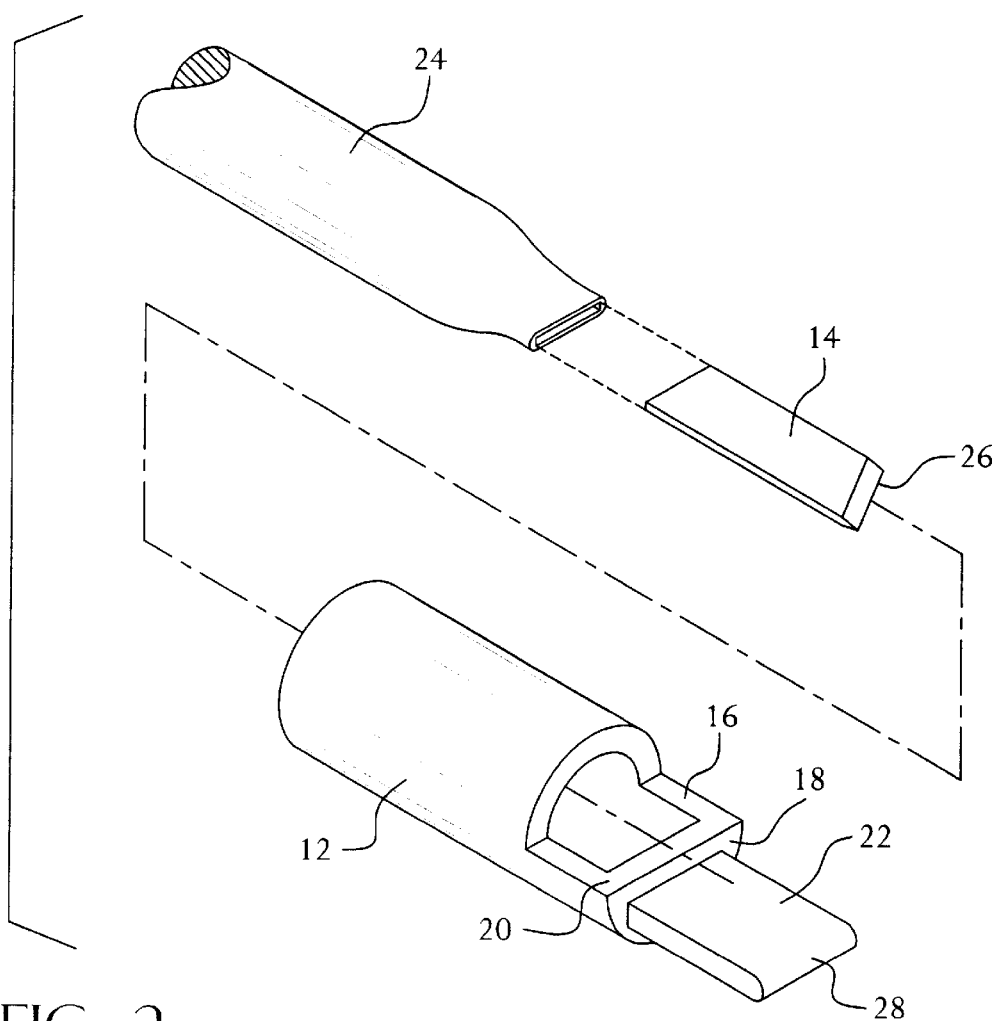
FIG. 2 is an exploded view of the surgical cutting device of FIG. 1.
Figure 3:
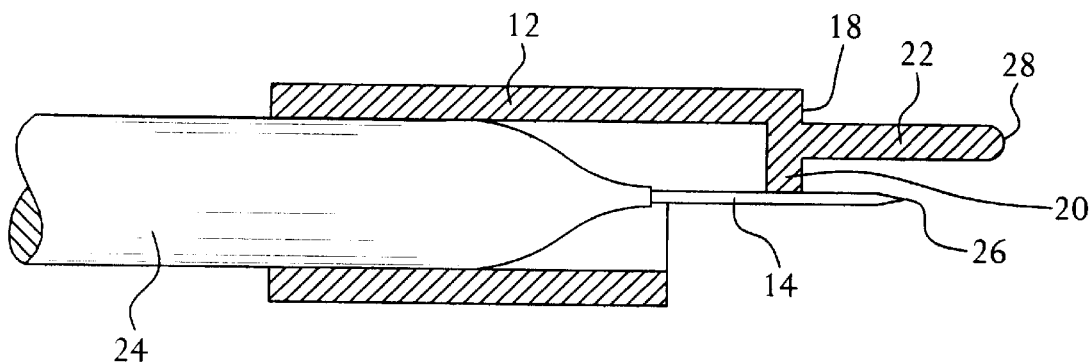
FIG. 3 is a side elevation view of the cutting device of FIG. 1, with the holder shown partially in section.
Figure 4:
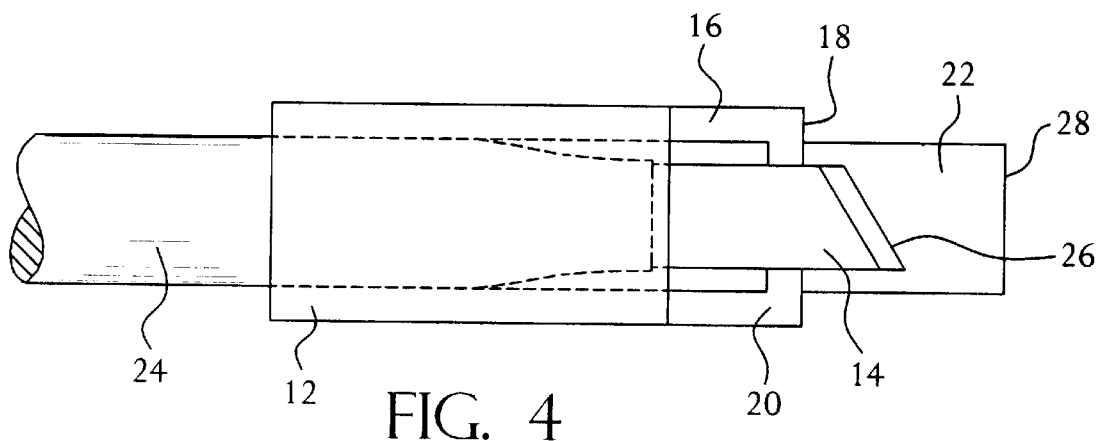
FIG. 4 is a top plan view of the device of FIG. 1.

As illustrated in FIG. 2, the cutting blade 14 may be mounted in a handle 24. The cutting blade 14 may be removable from the handle 24, so that it may be replaced by a new, sterile blade for each procedure, or it may be integral with the handle 24. As with the holder 14, the surface of the handle 24 may be knurled to assist the surgeon in grasping the handle and preventing it from slipping during use. The handle 24 is dimensioned to fit within the holder 12 for reciprocal movement along the longitudinal axis of the holder 12. Preferably bly, the outer diameter of the handle 24 is just slightly less than the inner diameter of the holder 12 and tapers toward the distal end thereof, so that the handle 24, and thus the cutting blade 14, can be linearly advanced and retracted with respect to the distal end 18 of the holder 12. The step 20, in addition to controlling the spacing between the cutting blade 14 and the applanation plate 22, serves to guide the cutting blade 14 for movement in a single plane and prevent the cutting blade 14 from rotating about its longitudinal axis while it is advanced. The step 20 also serves as a stop, so that the extent to which the blade 14 may be advanced into tissue relative to the distal end 18 can be limited. The step 20 thus cooperates with the handle 24 to prevent the cutting,blade 14 from being advanced beyond a preselected distance determined in part by the distance between the step 20 and the distal end of the handle 24. Other ways of guiding the handle 24 and the blade 14 with respect to the holder 12, such as a rib on the handle 24 and a slot on the inner surface of the holder 12 for receiving the rib, and other ways of limiting the extent to which the cutting blade 14 may be advanced, may also be provided without departing from the invention.

As will be appreciated, the cutting blade 14 is reciprocally movable with respect to the holder 12, and the cutting blade 14 moves in a linear fashion in and out of the holder 12. The cutting blade 14 may be advanced by moving the handle 24 by hand, such as by pushing it between finger and thumb, or by moving the handle 24 by an electric motor or mechanical device such as a gear, worm, or cable.

The device 10 may be made of any suitable materials. For example, the device 10 may be constructed of surgical grade steel, and may be sterilized and reused. Alternatively, only the blade 14 may be made of surgical steel, and the remainder of the device 10 may be made of a thermosetting plastic resin material, so as to be relatively inexpensive and disposable after use. The holder 12 may be a single integral piece, or may be made of two or more pieces assembled together. The dimensions of the device 10 and its constituent elements, and the extent to which the cutting blade 14 may be advanced, are chosen to accommodate the procedures for which the device 10 will be use. The cutting blade 14 preferably has a cutting edge 26 which is both beveled and angled with respect to the longitudinal axis of the blade, to facilitate cutting the tissue to be incised. However, any desired blade and edge configuration may be used, depending upon the tissue to be incised and the surgical procedure to be performed.

Figure 5:
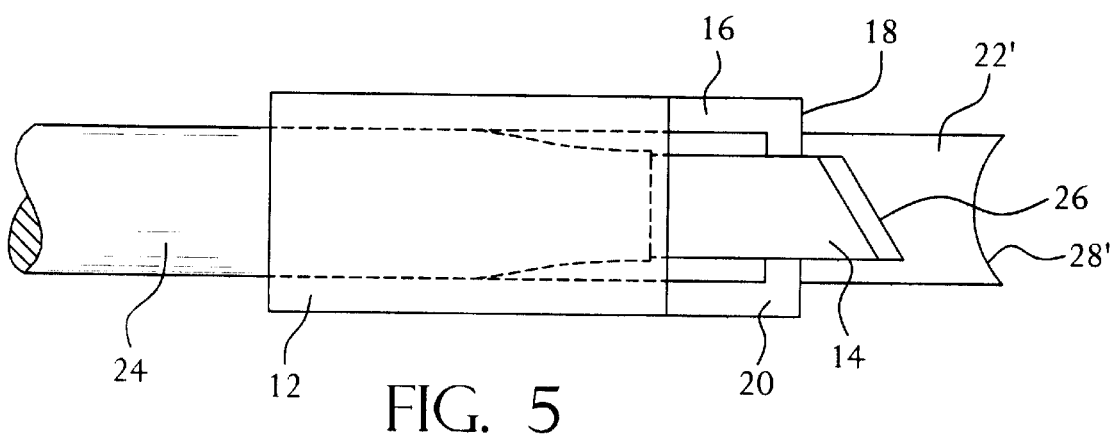
FIG. 5 is a top plan view of the device of FIG. 1, with an alternative configuration of applanation plate.
Figure 9:
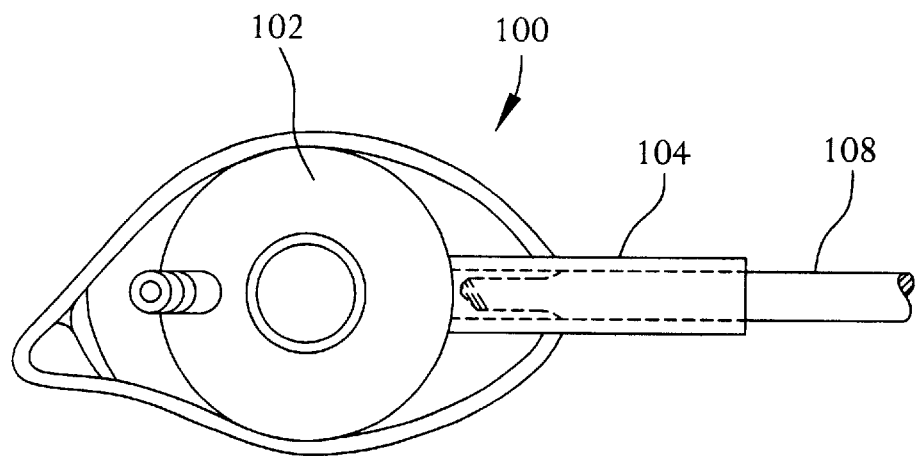
FIG. 9 is a top plan view of a second embodiment of a surgical cutting device according to the present invention showing a vacuum ring, a holder and a cutting blade.

The applanation plate 22 preferably has a bull nose, or rounded, end 28, which is placed in contact with tissue to be incised, as will be described in greater detail hereinafter. The end 28 of the applanation plate 22 may extend straight across, as shown in FIGS. 1 through 4, or may be concave, as shown in FIG. 5. The applanation plate 22' with a concave end 28' shown in FIG. 5 may be of particular utility in ophthalmic surgery, in that the curvature of the concave end 28' may assist the surgeon in placing the applanation plate 22' against the cornea and holding it in place when making the conjunctive flap. Other configurations of the end 28 of the applanation plate 22 useful in other surgical procedures may suggest themselves to those skilled in the art and are within the scope of the invention.

FIGS. 6 through 8 illustrate the use of the device 10 in ophthalmic surgery, although, as noted previously, the invention is not limited to any specific surgical procedure. In FIG. 6, the device 10 is illustrated in connection with making an incision into an eye 30 to create a conjunctive flap. The end 28 of the applanation plate 22 is placed against the cornea 32, and sufficient pressure is applied to the cornea to alter its pre-incision contour, as best seen in FIGS. 6 and 7. Preferably, the end 28 of the applanation plate 22 is placed in a location in the area of the limbus, so that the cutting edge of the blade 14 will incise the eye 30 at the corneal border. Once the device 10 has been placed in the desired location against the eye 30, and sufficient pressure applied to alter the contour of the cornea 32, the blade 14 is advanced into the cornea 32 by pushing handle 24 toward the eye, thus incising the cornea. After the incision is made, the blade 14 is retracted by pulling the handle 24 away from the eye.

Since the blade 14 moves linearly and in a single plane relative to the holder 12, the blade 14 makes an incision 34 which is also linear and lies in a single plane. However, the incision 34 is linear and planar with respect to the tissue only while its contour has been altered due to the pressure applied by the applanation plate 22. Once the applanation plate 22 is removed from the tissue, the tissue relaxes and returns to its pre-incision contour, as illustrated in FIG. 8. When it does so, the incision 34 assumes a multiplane, or stepped, shape as shown in FIG. 8. Thus, the device 10 makes it possible to form a stepped incision by merely advancing and retracting a cutting blade in a linear, planar fashion. No special surgical skills are required, and the resulting incision is precise and accurate. Moreover, the incision is repeatable from procedure to procedure, which gives the surgeon the ability to better anticipate the results of the procedure.

The depth of the incision into the tissue when the tissue is in its altered state, as illustrated in FIG. 7 (i.e., in ophthalmic surgery, the depth of the cataract groove) can be controlled by controlling the spacing between the applanation plate 22 and the cutting blade 14. The farther apart the applanation plate 22 and the cutting blade 14 are disposed, the deeper the incision will be before it changes direction to form the step. Where desired, an adjustment may be provided to enable the surgeon to selectably control the spacing.

Referring now to FIGS. 9-12, there is shown a surgical cutting device 100 according to another embodiment of the present invention. This embodiment is similar to the first embodiment described above, except for those features specifically described below. The cutting device 100 comprises a vacuum ring 102, a holder 104, and a cutting blade 106. The cutting blade 106 may be mounted in a handle 108. The handle 108 and the cutting blade 106 are linearly movable within the holder 104. The vacuum ring comprises an outer housing wall 110 and an inner contact wall 112. The contact wall 112 preferably has a concave shape. A hollow chamber 114 is formed between the housing wall 110 and the contact wall 112. The contact wall 112 includes a plurality of hollow passageways 116 between the hollow chamber 114 and an external surface of the contact wall 112. The device 100 also comprises a suction port 118 extending from the housing wall 110 of the vacuum ring 102. The suction port 118 includes an internal passage way 120 to the hollow chamber 114.

The contact wall 112 includes a blade passageway 122 which enables the blade 106 to pass through the contact wall 112 as the blade 106 and the handle 108 are moved linearly into the holder 104. The contact wall 112 further includes an applanation section 124 in close proximity to the blade passageway 122. Similar to the applanation plate 22 described above with respect to the first embodiment, the applanation section 124 contacts the tissue to be incised by the cutting blade 106, and is similarly shaped to alter the contour of the cornea.

Figure 10:
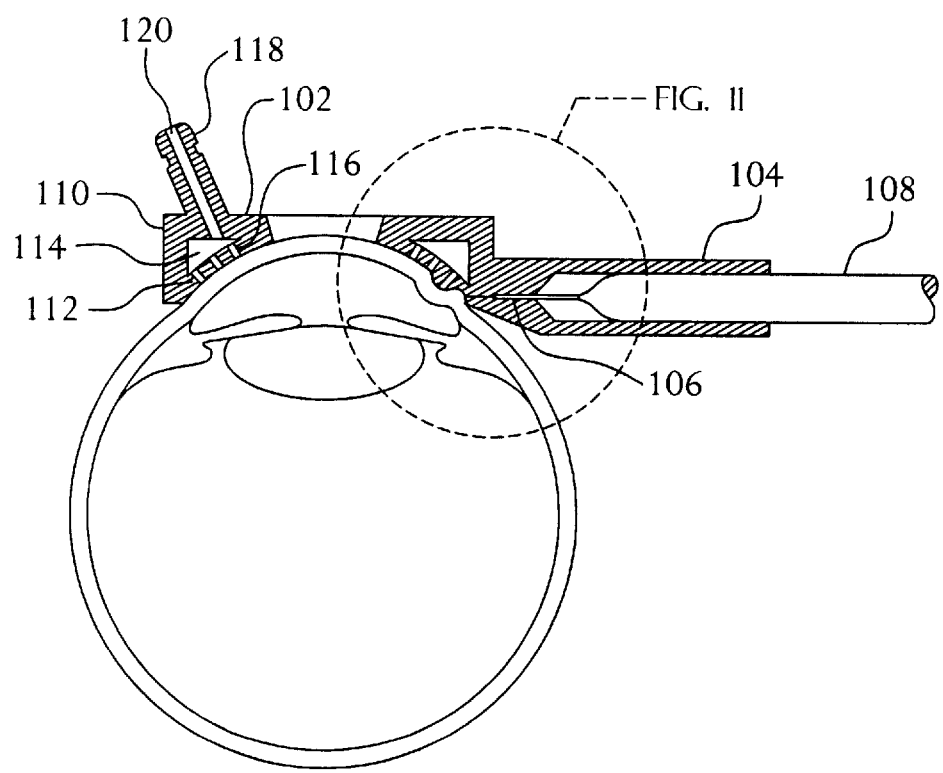
FIG. 10 is a section view of the device of FIG. 9, showing the applanation section.
Figure 11:
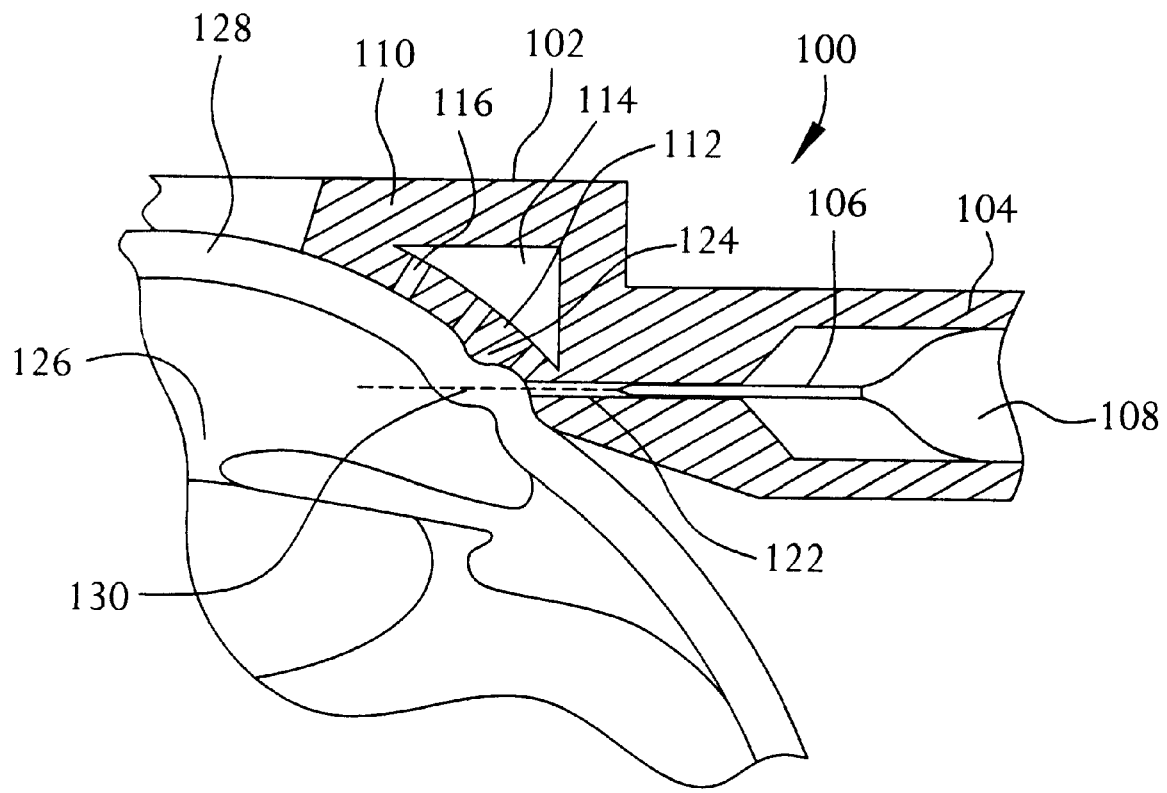
FIG. 11 is a section detail view of the device of FIG. 10 illustrating a linear incision effected in the cornea by the present invention, after the blade has been retracted and while the vacuum ring and applanation section are still in contact with the eye.

Referring particularly to FIGS. 10 and 11, the use of the device 100 is illustrated. Although those figures illustrate the use of the device 100 in opthalamic surgery, the present invention is not limited to any particular surgical procedure. In use, the suction port 116 is connected to a vacuum source (not shown). The vacuum ring 102 is placed against an eye 126. The vacuum source is activated to draw any air from the area between the contact wall 112 and the eye 126 through the passage ways 120 and the hollow chamber 114. As a result, the cornea 128 is drawn into engagement with the contact wall 112. As the cornea 128 engages the contact wall 112, the applanation section 124 applies sufficient pressure to alter the contour of the cornea 128. Once the contour of the cornea 128 is altered, the blade 106 is linearly advanced into the cornea 128 by pushing the handle 108 toward the eye 126, thus incising the cornea 128. After the incision is made, the blade 106 is retracted by pulling the handle 108 away from the eye 126.

Figure 12:
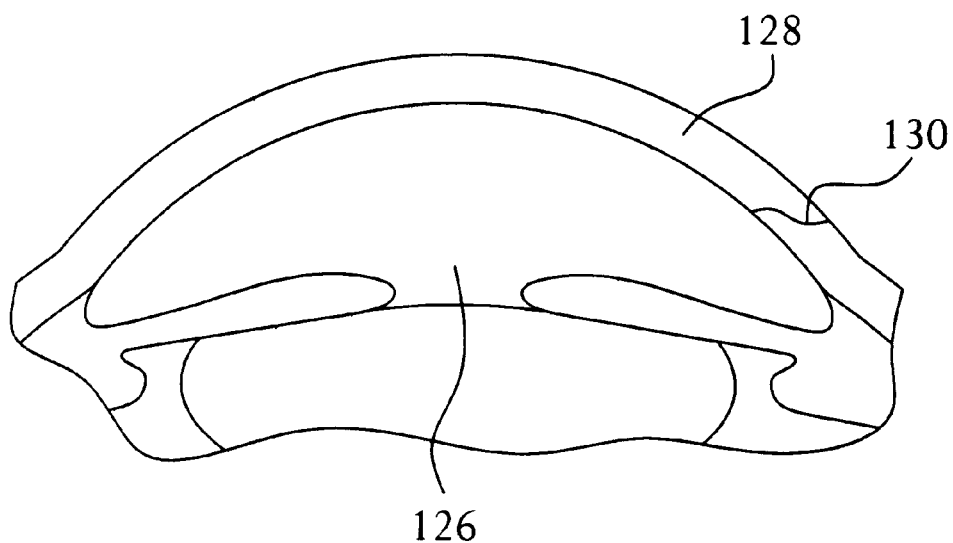
FIG. 12 illustrates the shape of the incision of FIG. 11 after the vacuum ring and applanation section have been removed and the eye allowed to return to its pre-incision contour.

Since the blade 106 moves linearly and in a single plane relative to the holder 104, the blade 106 makes an incision 130 which is also linear and lies in a single plane. However, the incision 130 is linear and planar with respect to the tissue only while its contour is altered due to the pressure applied by the applanation section 124. Once the vacuum is turned off and the applanation section 124 is removed from the tissue, the tissue relaxes and returns to its preincision contour, as illustrated in FIG. 12. When it does so, the incision 130 assumes a multiplane, or stepped, shape as shown in FIG. 12. Thus, the device 100 makes it possible to form a stepped incision by merely advancing and retracting a cutting blade in a linear, planar fashion. No special surgical skills are required, and the resulting incision is precise and accurate. Moreover, the incision is repeatable from procedure to procedure, which gives the surgeon the ability to better anticipate the results of the procedure.

The present invention may be embodied in other specific forms without departing from the spirit or essential attributes thereof and, accordingly, reference should be made to the appended claims, rather than to the foregoing specification, as indicating the scope of the invention.

What is claimed is:

1. A surgical cutting device, comprising
   a holder having a distal end,
   an applanation plate extending from said distal end for contacting and altering the contour of tissue to be incised, and
   a cutting blade reciprocally movable with respect to the holder and extending from said distal end in proximity to the applanation plate, the blade being guided by the holder and linearly advanceable into said tissue to effect an incision and retractable therefrom wherein the holder is generally in the form of a hollow tube, the distal end of the tube being partially closed by an end wall.

2. A surgical cutting device according to claim 1, wherein the applanation plate extends from the end wall, a portion of the end wall being located between the applanation plate and the cutting blade for spacing the cutting blade from the applanation plate by a preselected distance.

3. A surgical cutting device, comprising:
   a vacuum ring including an inner contact wall and an outer housing wall, the contact wall and the housing wall forming a hollow chamber therebetween, the contact wall including an applanation section extending therefrom for contacting and altering the contour of tissue to be incised and a passageway adjacent the applanation section;
   a holder extending from the housing wall; and
   a cutting blade reciprocally and linearly movable with respect to and guided by the holder through the passageway and into the tissue to effect an incision therein in proximity to the applanation section.

4. A surgical cutting device according to claim 3, further comprising a suction port, connectable to a source of suction, including a passageway connected to the hollow chamber and at least one passageway in the contact wall connected to the hollow chamber, the suction port passageway, the hollow chamber, and the contact wall passageway providing a pathway for evacuating any material between the tissue and the contact wall to create a vacuum therebetween.

* * * * *